United States Patent [19]

Guinn et al.

[11] Patent Number: 4,894,342
[45] Date of Patent: Jan. 16, 1990

[54] BIOREACTOR SYSTEM

[75] Inventors: Perry W. Guinn, Oregon City; Gary N. Mills, Gladstone, both of Oreg.

[73] Assignee: C. D. Medical, Inc., Miami Lakes, Fla.

[21] Appl. No.: 909,962

[22] Filed: Sep. 22, 1986

Related U.S. Application Data

[63] Continuation-in-part of Ser. No. 862,014, May 12, 1986.

[51] Int. Cl.⁴ .................... C12M 1/04; C12M 1/14; C12M 1/34
[52] U.S. Cl. ...................... 435/291; 435/240.242; 435/284; 435/285; 435/313; 435/813; 435/818
[58] Field of Search .................. 435/240.242, 813, 818, 435/284, 285, 291, 313

[56] References Cited

U.S. PATENT DOCUMENTS

| | | |
|---|---|---|
| 3,407,120 | 10/1968 | Weiss et al. |
| 3,734,851 | 5/1973 | Matsumura |
| 3,821,087 | 6/1974 | Knazek et al. |
| 4,087,327 | 5/1978 | Feder et al. |
| 4,116,778 | 9/1978 | Belousov et al. ............ 435/291 |
| 4,266,026 | 5/1981 | Breslau |
| 4,335,215 | 5/1982 | Tolbert et al. |
| 4,411,651 | 10/1983 | Schulman |
| 4,440,853 | 4/1984 | Michaels |
| 4,530,759 | 7/1985 | Schal |
| 4,559,299 | 12/1985 | Rotman ................... 435/240.242 |
| 4,725,148 | 2/1988 | Endo et al. ............... 435/291 |

FOREIGN PATENT DOCUMENTS

| | | |
|---|---|---|
| 60-126075 | 7/1985 | Japan |
| WO86/02378 | 4/1986 | PCT Int'l Appl. |
| WO86/02379 | 4/1986 | PCT Int'l Appl. |

OTHER PUBLICATIONS

Endotronics brochure "ACUSYST-JR." 1986, 8500 Evergreen Blvd., Coon Rapids, MN 55433.
Endotronics brochure "ACUSYST-M".
Endotronics brochure "ACUSYST-S".
AMICON brochure, publication No. 492, 17 Cherry Hill Drive, Danvers, MA 01923.
"VIRTIS Omni-Culture Laboratory Fermenter" brochure, 1984/10M, Gardner, NY 12525.
Ventrex "Cellift" brochure, 1986, 217 Reed St., Portland, ME 04103.
Queue Systems brochure "The New Bioreactor System for Fermentation and Cell Culture" 1986, Parkersburg, WV, 26102, Box 1901.
Queue Systems brochure "New Technologies and Products for Cell Culture", 1985, Box 1901, Parkersburg, WV, 26102.
Queue Systems brochure (untitled) discussing Hybrinet Hollow Fiber Perfusion Bioreactor, 1986.

(List continued on next page.)

Primary Examiner—Barry S. Richman
Assistant Examiner—Timothy M. McMahon

[57] ABSTRACT

An improved bioreactor system for culturing cell products is disclosed in which novel system components are employed to reduce cost and increase reliability. The system includes a simple in-line heater for heating the nutrient fluid, thereby obviating the need for an expensive incubator. Gas bubbles formed during the heating of the nutrient fluid are removed by a novel gas trap that requires no operator intervention. A humidifier humidifies an aerating gas before it is passed through an oxygenator, thereby preventing water within the nutrient fluid from evaporating, with a consequent increase in nutrient fluid concentration. The operation of the humidifier is efficiently combined with that of a nutrient fluid heat exchanger so that a pump is not required to circulate the heat exchanger water bath. The system further includes a valve and pump arrangement whereby fresh nutrient fluid can periodically be introduced and spent nutrient fluid periodically drained without operator intervention. Observation of the color of the nutrient fluid from a concealed location within the bioreactor enclosure is also made possible.

6 Claims, 4 Drawing Sheets

POLYMER B        POLYMER A
                 WITH CARBON BLACK

OTHER PUBLICATIONS

Queue/Monsanto brochure "Hybrinet Hollow Fiber Bioreactor," 1986, Box 1901, Parkersburg, WV, 26102.

B. Braun brochure "Biostat M, the Mini-Fermenter for Small Volumes".

L. H. Fermentation, Ltd. brochure "2000 Series Fermenter Range".

Cooney, "Bioreactors: Design and Operation," *Science*, vol. 219, pp. 728-733, 1983.

Tharakan and Chau, "A Radial Flow Hollow Fiber Bioreactor for the Large-Scale Culture of Mammalian Cells," *Biotechnology and Bioengineering*, vol. XVIII, pp. 329-342, (1986).

Feder and Tolbert, "The Large-Scale Cultivation of Mammalian Cells," *Scientific American*, vol. 248, pp. 36-43, Jan., 1983.

Prenosil and Pedersen, "Immobilized Plant Cell Reactors," *Enzyme Microb. Technol.*, vol. 5, pp. 323-331, Sep., 1983.

Park and Kim, "Hollow-Fibre Fermenter Using Ultrafiltration," *Applied Microbiology and Biotechnology*, vol. 22, pp. 190-194, 1985.

Ku, Kuo et al., "Development of a Hollow-Fiber System for Large-Scale Culture of Mammalian Cells," *Biotechnology and Bioengineering*, vol. XXIII, pp. 79-95, (1981).

POLYMER A WITH CARBON BLACK

POLYMER B

SBS    PS WITH CARBON BLACK

POLYMER B     POLYMER A WITH PAC

FIG. 5
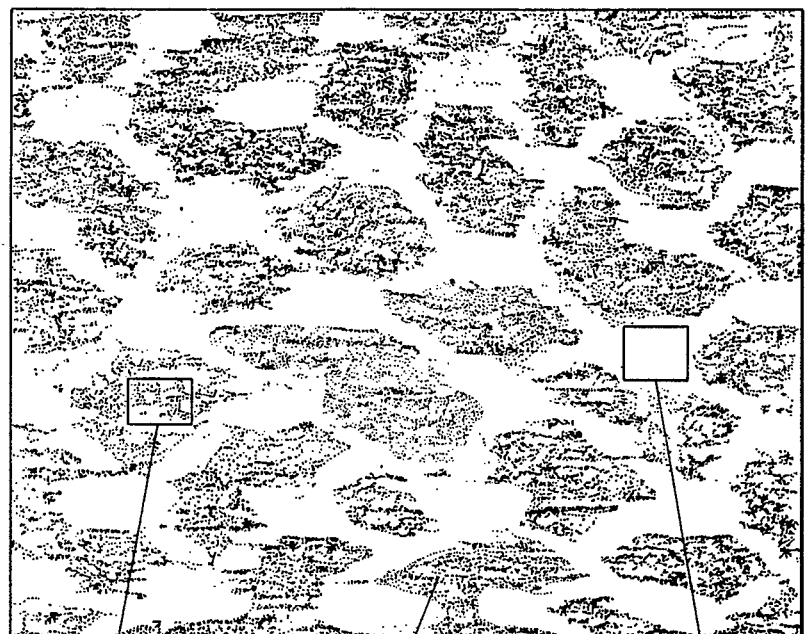
FIG.6.    POLYMER B    FIG.7.
POLYMER B
POLYMER A WITH PAc
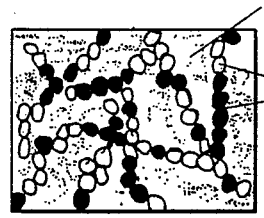
FIG. 6
POLYMER A WITH PAc
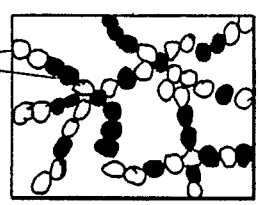
FIG. 7

BIOREACTOR SYSTEM

RELATED APPLICATION

This application is a continuation-in-part of copending application Ser. No. 862,014 filed May 12, 1986 and entitled Bioreactor Apparatus, which application is incorporated herein by reference.

BACKGROUND OF THE INVENTION

This invention relates to bioreactor systems and to the fluid processing and sensing components used in such systems.

Bioreactor systems are increasingly being used for the synthesis of biological products. An exemplary bioreactor system employs a hollow fiber bioreactor cartridge having a multitude of semipermeable fibers that serve as a support and a nutrient conduit for cell culture. Cells are typically grown on the outside of the semipermeable fibers and are maintained by perfusion of nutrient medium which is circulated within the fibers. Waste products excreted by the cultured cells perfuse into the fibers and are carried away in the nutrient medium. Desirable cellular by-products, such as monoclonal antibodies, are typically too large to perfuse into the fibers and are thus trapped in the extracapillary region of the bioreactor cartridge.

The process control tasks associated with operation of a bioreactor system are very demanding. In many applications, the desired cell by-products are produced at an extremely slow rate. Sometimes the system must operate continuously for weeks or months at a time in order to accumulate a fraction of a gram of usable product. Any malfunction in the system can have long lasting repercussions on a project. Accordingly, it is crucial that all process control components be able to work continuously and reliably for extended periods of time with a minimum of human supervision and intervention.

The reliability of prior art bioreactors suffers by reason of the complex subsystems typically incorporated therein. An exemplary system may include a large incubator and three or more pumps. One pump is used to circulate nutrient fluid from a reservoir through the bioreactor. A second pump is used to add fresh nutrient fluid to the reservoir. A third pump is used to remove spent nutrient fluid from the reservoir. A fourth pump is used to circulate a warm water bath which surrounds the nutrient fluid reservoir. Such complicated systems are inherently susceptible to reliability problems when operated over extended periods of time.

Related to the reliability concern is that of maintaining absolute sterility. The introduction of virtually any foreign body into the system will fatally disrupt its operation. Accordingly, it is desirable that bioreactor design be oriented so as to minimize opportunities for the system to become contaminated.

Accordingly, a need remains for improved bioreactor systems.

SUMMARY OF THE INVENTION

It is an object of the present invention to provide a reliable bioreactor system.

It is another object of the present invention to provide an inexpensive bioreactor system.

It is a further object of the present invention to provide a bioreactor system which need not be operated in an incubator.

It is still another object of the present invention to trap air bubbles released from heated nutrient fluid before they can be introduced into the fibers of a bioreactor cartridge.

It is yet another object of the present invention to provide an improved apparatus for introducing fresh nutrient fluid into, and removing spent nutrient fluid from, a bioreactor system.

It is still another object of the present invention to provide an improved apparatus for replacing fluid lost from a humidifier in a bioreactor system.

It is yet another object of the present invention to provide an improved apparatus for detecting the level of nutrient fluid in a bioreactor nutrient fluid reservoir.

It is still another object of the present invention to efficiently combine the operations of a humidifier and a heat exchanger in a bioreactor system.

It is yet another object of the present invention to detect remotely the color of a nutrient fluid in a nutrient fluid vessel concealed within a bioreactor system.

The foregoing and additional objects, features and advantages of the present invention will be more readily apparent from the following detailed description of a preferred embodiment thereof, which proceeds with reference to the accompanying drawings.

BRIEF DESCRIPTION OF THE DRAWINGS

FIG. 5 shows an air trap used in the bioreactor system of FIG. 1.

FIG. 6 shows an alternative embodiment of the air trap of FIG. 5.

FIG. 7 shows a nutrient fluid color sensing apparatus used in the bioreactor system of FIG. 1.

DETAILED DESCRIPTION

Figure 1:
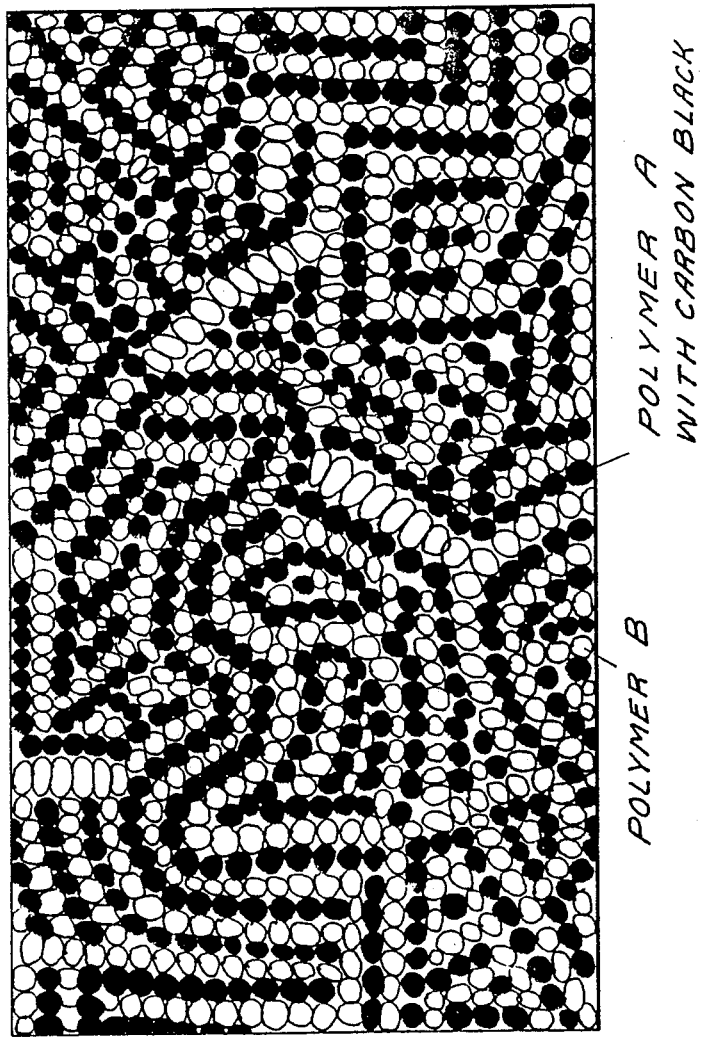
FIG. 1 shows a schematic diagram of a bioreactor system according to the present invention.
Figure 2:
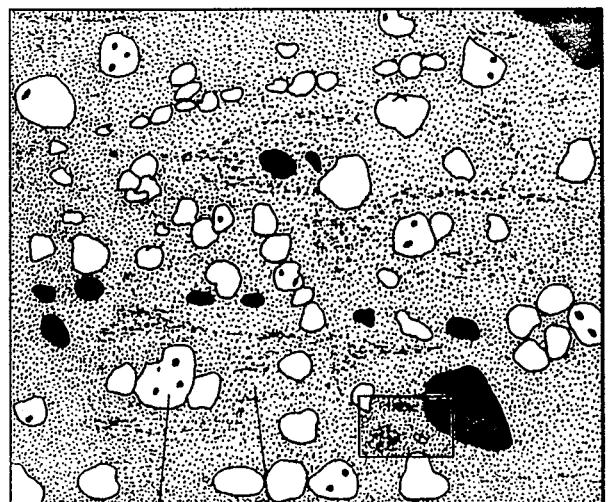
FIG. 2 shows a physical embodiment of the bioreactor system of FIG. 1.

With reference to FIGS. 1 and 2, one embodiment of a bioreactor system 10 according to the present invention includes a fluid reservoir 12, a pump 14 and a bioreactor 16. Nutrient media fluid 18 from reservoir 12 is pumped by pump 14 through bioreactor 16 and is returned to reservoir 12.

Bioreactor 16 typically comprises a plurality of semipermeable fibers or capillaries mounted within a cartridge. The nutrient fluid flows through the lumen of the fibers and perfuses to the extracapillary space. The cells to be cultured are typically placed in the extracapillary region and are nourished by the perfusion of nutrient through the semipermeable membrane. The bioreactor 16 included in one particular embodiment allows transfer of materials having a molecular weight up to 90,000 and includes an extracapillary region surface area of 1.3 square meters.

In FIG. 1, the lumen ports which communicate with the opposite ends of the bioreactor fibers are marked 20 and 22. The extracapillary ports, which communicate with the extracapillary region surrounding the bioreactor fibers, are marked 24 and 26. It is through these extracapillary ports that the cell culture is typically introduced at the beginning of an experiment and through which harvested cellular by-products are withdrawn.

In more detail, illustrated bioreactor system 10 includes a media output tube 28 extending within reservoir 12 for coupling the nutrient media within reservoir 12 to recirculation pump 14. A conduit 32 couples the output of pump 14 to an oxygenator 34 which serves to aerate the nutrient fluid with a controlled mixture of gasses.

Recirculation pump 14 is desirably reversible so that any air inadvertently introduced into the system during priming can be controllably withdrawn.

Oxygenator 34 can comprise a membrane device in which the nutrient fluid 18 circulates along one side of a membrane and the aerating gas passes along the second side. In the illustrated embodiment, oxygenator 34 is supplied with aerating gas from a humidifier/heat exchange apparatus, described below, through a conduit 36, a sterile filter 35 and a gas inlet port 134. Gas is expelled from oxygenator 34 through a gas outlet port 136 and is routed through a conduit 138 to a pressure gauge 140, a back pressure regulator 142 and a vent output 144. Back pressure regulator 142 is adjusted to obtain the desired gas pressure in oxygenator 34.

After aeration in oxygenator 34, the nutrient fluid is coupled through a conduit 38 to an in-line heater unit 40. Heater 40 is a simple resistive heater that obviates the need for the large incubators in which prior art systems are typically enclosed, this reducing system cost and increasing reliability.

A thermostatic control system 39 maintains the temperature of the nutrient fluid passing through heater 40 at a preset temperature, for example, 37 degrees Celsius. The temperature sensor used in the thermostatic control system is preferably positioned at the heater output so as to indicate most accurately the temperature of the fluid introduced to bioreactor 16.

Heater 40 is obscured in FIG. 2 by a removable tray 41 on which all of the fluid circuitry is mounted. Tray 41 enables the entire fluid processing circuitry of apparatus 10 to be removed and autoclaved as a unit. In the illustrated embodiment, heater 40 is substantially flat and is mounted below tray 41, thereby warming the fluid components mounted thereon.

After being heated by heater 40, the nutrient fluid 18 is passed through an air trap 42 and through a short conduit 44 to the inlet port 20 of bioreactor 16. The nutrient fluid perfuses through the fibers of bioreactor 16 and nourishes the cells contained therein. From the output port 22 of bioreactor 16, the nutrient fluid is coupled through a conduit 46, a junction 48 and a conduit 50 to a media return tube 52 within reservoir 12, thereby completing its circulation through the main bioreactor circulatory path 54. Media return tube 52 extends below the fluid level within media reservoir 12 so as to prevent the foaming of the proteinaceous nutrient as it returns to the reservoir. The ends of media return tube 52 and media output tube 28 within reservoir 12 are angled horizontally so as to induce a spiral fluid flow within the reservoir. This flow serves to mix the media and prevent its thermal stratification.

As nutrient fluid 18 circulates through bioreactor 16, the cell culture depletes certain nutrient components from the fluid and adds waste products to it. Accordingly, it is important that the nutrient fluid be refreshed to assure satisfactory cell culture. In the present invention, this can be effected by alternately withdrawing used nutrient fluid from the bioreactor circulation path 54 and replacing it with fresh nutrient fluid. This is preferably accomplished with the use of a pump 60 and an automatic system controller unit 62.

Illustrated pump 60 comprises a dual channel reversible peristaltic pump having a diameter of approximately five inches. The first pump channel comprises a deformable tube 68 linking a fresh fluid inlet 64 to a fresh fluid input circuit 70 in bioreactor apparatus 10. The second pump channel comprises a deformable tube 72 coupling a used fluid outlet 66 to a used fluid output circuit 74 in bioreactor system 10.

In the illustrated embodiment, the operational speed of pump 60 and the diameter of tubes 68 and 72 are selected so as to produce a flow rate through tubes 68 and 72 of approximately 17 milliliters per minute during operation of the pump.

A check valve system 76 is employed in connection with pump 60 to automatically open and close the various fluid paths within the fresh fluid and spent fluid circuits so as to allow the proper operation of said circuits at the appropriate times. When pump 60 is operating in the first direction, check valve system 76 allows the pump to pump fresh nutrient fluid from a source of fresh nutrient fluid, coupled to fresh nutrient fluid inlet 64, to fresh nutrient fluid input circuit 70. Fresh nutrient fluid input circuit 70 in turn couples fresh fluid to circulatory path 54 through a heat exchanger apparatus 100 described below. When pump 60 is operating in the first direction, check valve system 76 prevents the pump from pumping fluid from used fluid outlet 66 to the used fluid output circuit 74.

When pump 60 is operating in the second direction, check valve system 76 allows pump 60 to pump used fluid from the used fluid output circuit 74 to a used fluid drain connected to used fluid outlet 66. Used fluid output circuit 70 is coupled to a junction 48 in main circulating path 54. When pump 60 is operating in the second direction, check valve system 76 prevents the pump from pumping fluid from fresh fluid input circuit 70 to fresh fluid inlet 64.

In more detail, check valve system 76 includes a first check valve 78 serially connected in first tube 68 for permitting fluid flow in fresh fluid input circuit 70 when pump 60 is operated in the first direction, but not when the pump is operated in the second direction. A second check valve 80 is serially connected in second tube 72 for permitting fluid flow in the used fluid output circuit 74 when pump 60 is operated in the second direction, but not when pump 60 is operated in the first direction.

To prevent a build-up of pressure in whichever of first tube 68 or second tube 72 is blocked by the corresponding check valve 78, 80, third and fourth check valves, 82 and 84 are provided. Third check valve 82 is shunted across first tube 68 as it enters and exits peristaltic pump 60 and provides a circulatory path for fluid in the first tube when pump 60 is operated in the second direction. Fourth check valve 84 is shunted across second tube 72 as it enters and exits the peristaltic pump 70 and provides a circulatory path for fluid in the second tube when pump 60 is operated in the first direction.

It is important that check valves 78, 80, 82, 84 have a cracking pressure that is greater than the hydrostatic heads to which they might be subjected. For example, if the source of fresh nutrient fluid is elevated several feet above valve 82, it will present a hydrostatic head which will tend to open the valve. Similarly, if the waste fluid drain container is on the floor beneath valve 84, a hydrostatic head will again tend to open the valve. A cracking pressure of 4 p.s.i. for valves 78–84 is generally adequate.

By the above described valve arrangement, fluid paths are automatically opened and closed, as necessary, so that fluid can be added to and removed from the system without complicated electrical control systems and without human intervention.

OPTICAL LEVEL SENSORS

As noted above, pump 60 is operable in first and second directions to add fresh nutrient to, or remove spent nutrient fluid from, bioreactor apparatus 10. In the preferred embodiment, this is effected automatically by system controller 62. System controller 62 periodically energizes pump 60 in its second direction until a desired amount of used fluid has been withdrawn from the system. It thereafter energizes pump 60 in its first direction until a corresponding amount of replacement fresh fluid has been added to the system. By this technique, the volume of nutrient fluid 18 in the system is maintained relatively constant and is kept refreshed. System controller 62 includes means for effecting such operation on a periodic basis, such as hourly, so that a predetermined amount of fluid, such as 100 milliliters, is refreshed each period.

Figure 3:
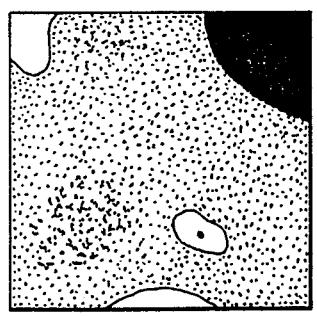
FIG. 3 shows an optical level sensing apparatus used in the bioreactor system of FIG. 1.

In the preferred embodiment, automatic system controller 62 is coupled to one or more devices which monitor the volume of fluid in fluid reservoir 12. In the illustrated embodiment, these volume monitoring devices comprise first and second level sensors 200, 202. With reference to FIGS. 1 and 3, each of level sensors 200, 202 includes an elongated optical conductor 204 extending into reservoir 12. Optical conductor 204 has a cylindrical body portion 206, a first, planar end 208 and a second, right-angled conical end 210. If the liquid in reservoir 12 is below a certain level, conical end 210 is surrounded by a gas. If the liquid level in the reservoir is above a certain level, conical end 210 is in contact with nutrient fluid.

Although illustrated sensor 200 has a cylindrical body portion, other geometries, such as rectangular, could alternatively be employed. The cylindrical shape was chosen to simplify the seal through which sensor 200 extends through the top of reservoir 12.

An optical transmitter 212, such as a light emitting diode, is coupled to planar end 208 of optical conductor 204 for transmitting energy through the optical conductor toward conical end 210. An optical receiver 214, such as a photodetector, is also coupled to planar end 208 of optical conductor 204 and receives energy transmitted by transmitter 212 and reflected from the conical end 210. This reflected energy has a first magnitude when conical end 210 is surrounded by a gas, and has a different magnitude when the conical end is in contact with the nutrient fluid. A detector 216 is coupled to optical receiver 214 by a cable 218 and detects the magnitude of energy received by the optical receiver. A detection of the first magnitude of energy by detector 216 indicates that the fluid level in reservoir 12 is below a certain point. The detection of a different magnitude of energy by detector 216 indicates that the fluid level within reservoir 12 is above a certain point. Level sensors 200, 202 are thereby able to detect the liquid level in reservoir 12.

In the preferred embodiment, the conical end of detector 200 extends to a first level within reservoir 12 and the conical end of detector 202 extends to a second reference level. Detectors 200 and 202 thus indicate whether or not the nutrient level in reservoir 12 is above or below these levels. Normally, reservoir 12 is maintained so that the level of fluid nutrient 18 is slightly above the second level. Periodically, such as once an hour, system controller 62 causes reversible pump 60 to begin operation in its second mode so as to reduce the level of fluid in reservoir 12. System controller 62 allows this withdrawal of spent fluid to continue until first level detector 200 indicates that the level of nutrient fluid in the reservoir has fallen below the first level. At this point, system controller 62 causes reversible pump 60 to switch to its first direction and add fresh fluid to bioreactor apparatus 10. Operation of reversible pump 60 in this first mode is continued until system controller 62 determines, through second level detector 202, that the level of fluid in reservoir 12 has returned to its initial, second level. At this point, system controller 62 causes reversible pump 60 to return to its idle state for the remainder of the illustrative hour.

In alternative embodiments, a single level sensor is substituted for the two illustrated in FIG. 1. For example, just level sensor 202 is employed. In such embodiment, pump 60 is operated in its second direction for a period to expel spent fluid. This period can be set to correspond to the removal of a desired volume of spent nutrient by a timer or by an encoder which monitors the number of revolutions of peristaltic pump 60. Thereafter, pump 60 is switched to its first direction and is operated until sensor 202 indicates that the level of fluid in reservoir 12 has returned to its "full" level. Pump 60 then ceases operation until controller 62 causes the cycle to begin again.

In the above described refresh techniques, a single pump serves the purpose of two pumps in the prior art, thereby increasing system reliability and decreasing system cost. System reliability is further increased by the low duty cycle at which pump 60 is operated, thus extending the lifetimes of tubes 63, 72 used therein. In other embodiments of the present invention, reversible pump 60 can be replaced by two single direction pumps which are also operated at very low duty cycles, substantially increasing their reliability. Since the rate at which the fresh fluid is added and spent fluid withdrawn is not critical, an inexpensive one-speed A.C. operated peristaltic pump can be used, further reducing costs over prior art systems which use variable speed D.C. pump technology.

Desirably, automatic system controller 62 is an electronic control unit. Alternately, the components monitored and controlled by system controller 62 can be monitored and controlled manually.

HUMIDIFIER/HEAT EXCHANGER

Figure 4:
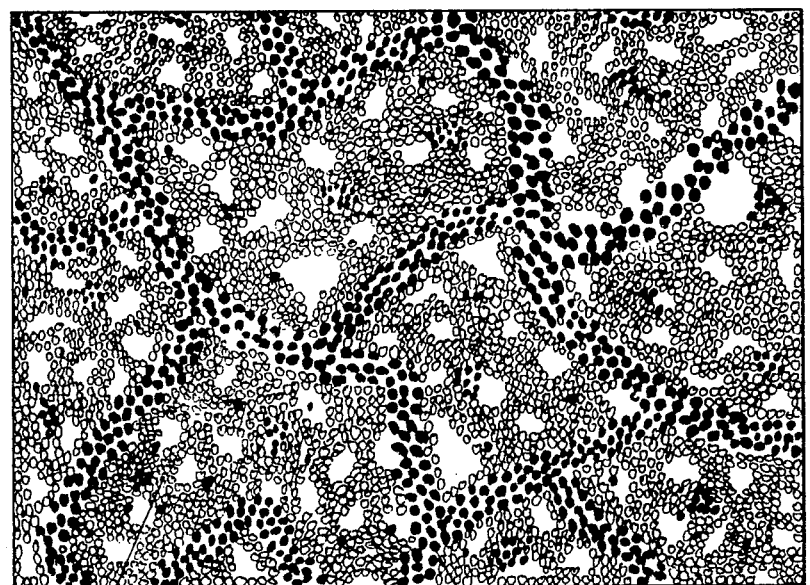
FIG. 4 is a sectional view of a combination humidifier/heat exchanger apparatus used in the bioreactor system of FIG. 1.
Figure 1:
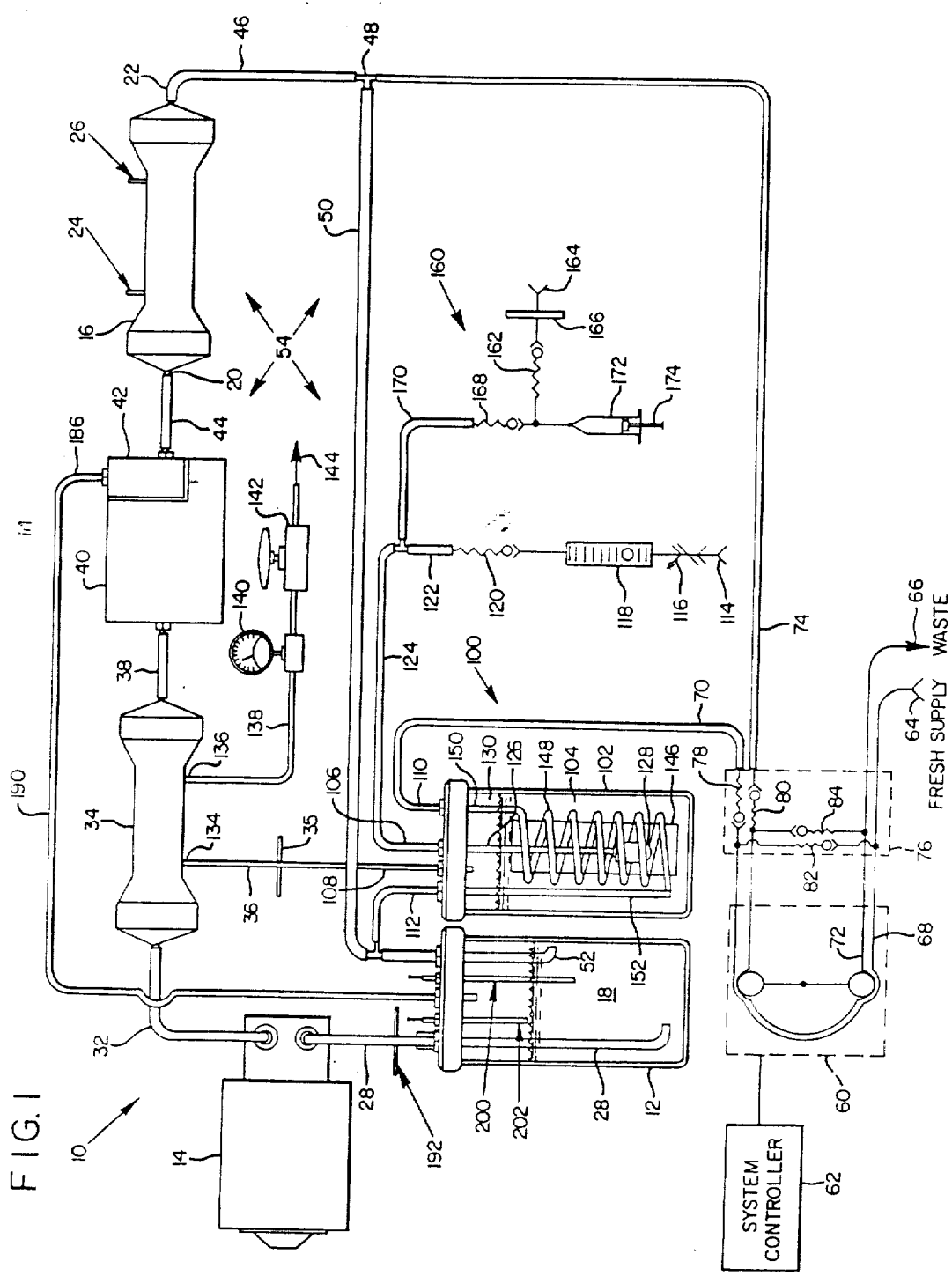
Figure 2:
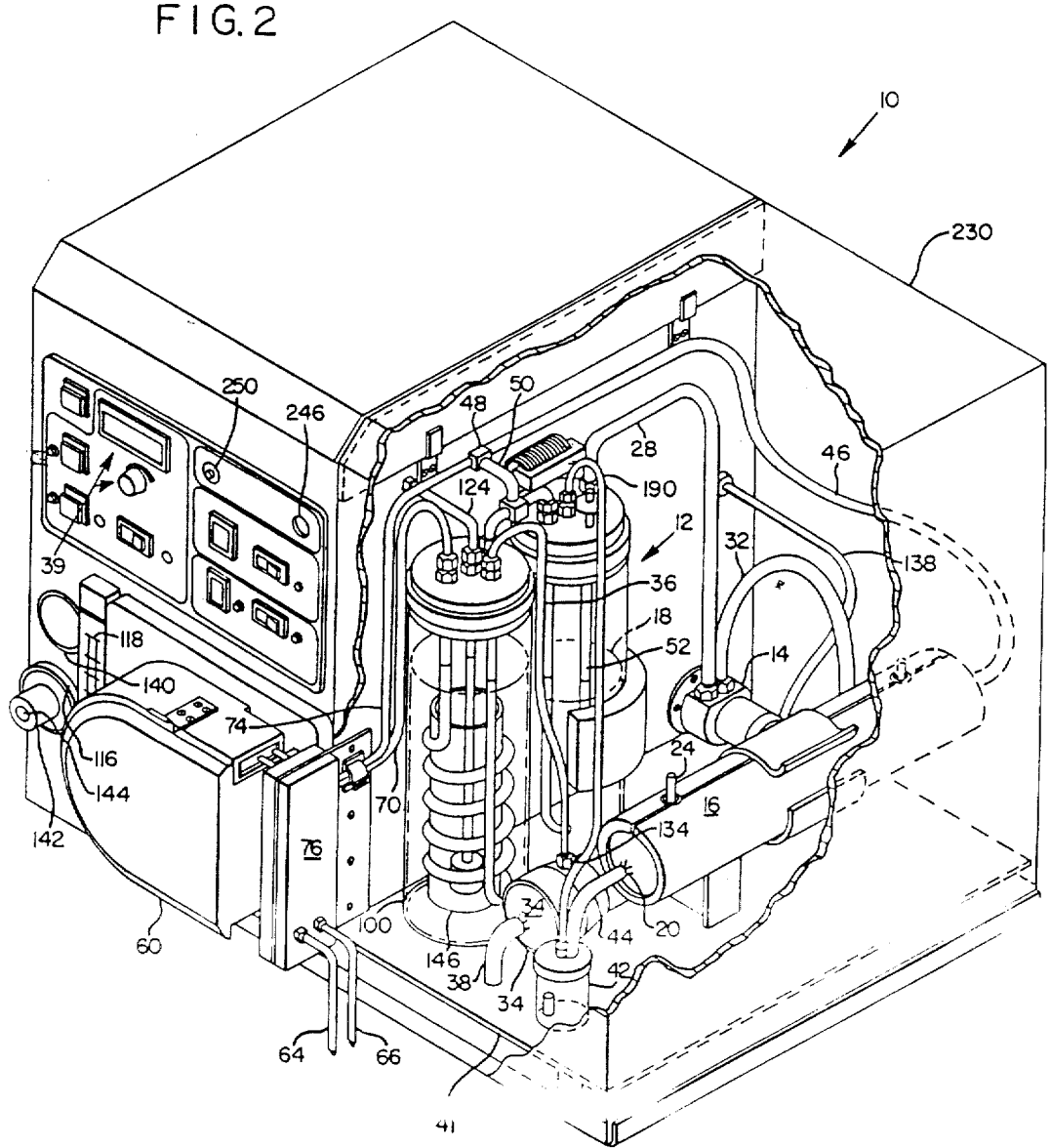
Figure 8:
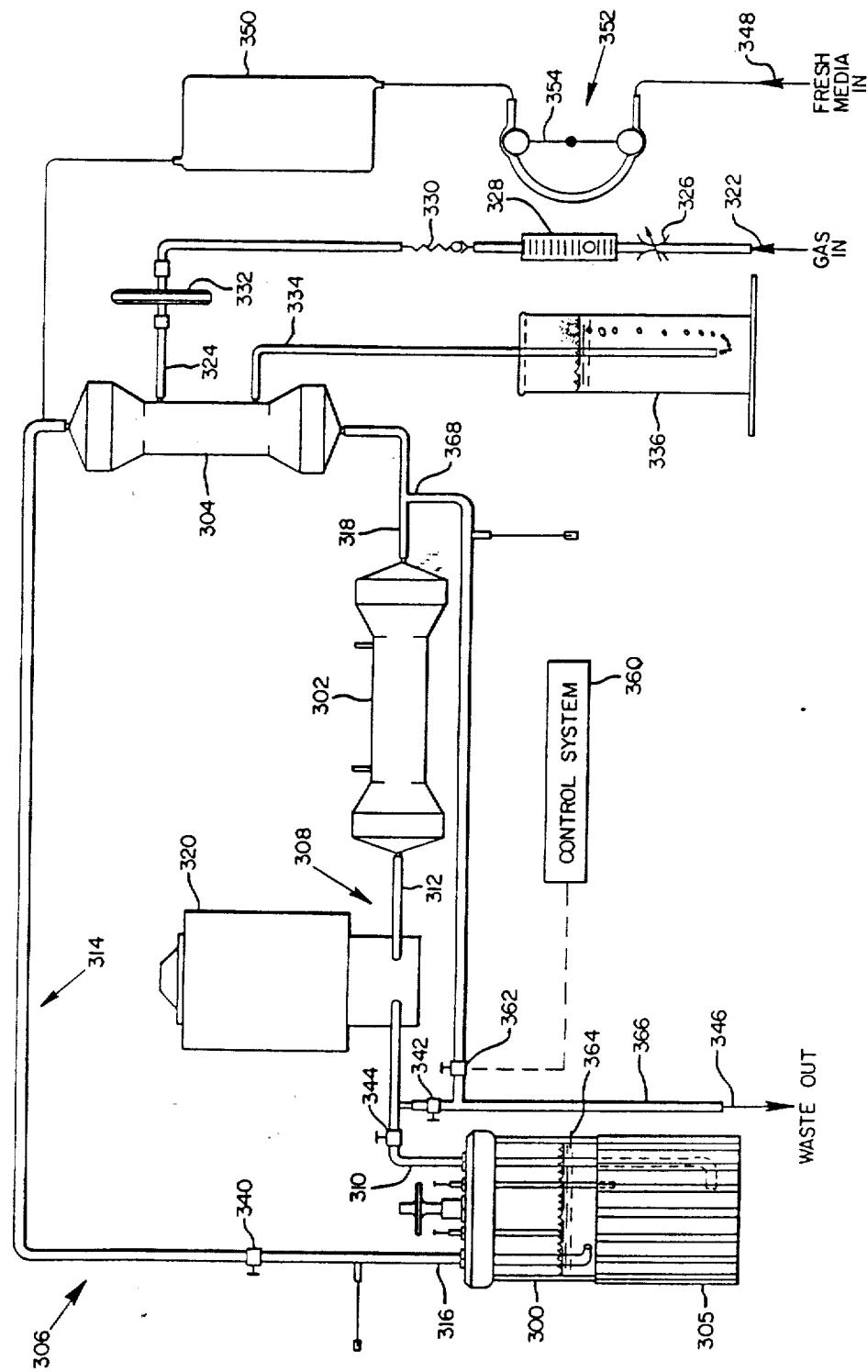

It is desirable that fresh nutrient fluid introduced at fresh fluid inlet 64 be warmed somewhat before it is added to reservoir 12 so as to prevent excursions in reservoir temperature. It is also desirable that the aerating gas provided to oxygenator 34 be warmed and humidified. Warming the gas maintains thermal stability within the system. Humidifying the gas prevents changes in the concentration of the nutrient fluid which would otherwise occur if water in the nutrient were allowed to evaporate into dry aerating gas and be vented to the atmosphere. To implement both of these functions, a novel humidifier/heat exchanger apparatus 100 is provided and is illustrated in FIG. 4.

Humidifier/heat exchanger apparatus 100 comprises a vessel 102 for containing a fluid 104, such as deionized reverse osmosis water. At the top of apparatus 100 are provided a gas inlet port 106, a gas outlet port 108, a nutrient fluid inlet port 110 and a nutrient fluid outlet port 112.

Gas for oxygenator 34 is introduced at a gas inlet 114 and routed through a control valve 116, a flow meter 118, a check valve 120 and conduits 122 and 124 to gas inlet port 106 on apparatus 100. Gas introduced at gas inlet port 106 is carried into a lower region of vessel 102 by a conduit 126 and is terminated at a stainless steel sintered filter 128. Conduit 126 and sintered filter 128 are coupled by a connector member 129. Sintered filter 128 transforms the gas flow into a multitude of tiny bubbles, which then rise through fluid 104 to a gas-containing region 130 at the top region of vessel 102. As the bubbles rise through fluid 104, the gas contained therein is humidified. This humidified gas is then carried from region 130 through gas outlet port 108, conduit 36 and filter 35 to a gas inlet port 134 on oxygenator 34.

An aquarium air stone or other very fine filter mesh can be substituted for illustrated stainless steel sintered filter 128.

In the preferred embodiment, a cylindrical tube 146 is vertically disposed in the lower region of vessel 102 and extends into the upper region. Cylindrical tube 146 is open at locations in the upper and lower regions to allow the circulation of fluid through the tube from the lower region to the upper region. Bubbler 128 is disposed within tube 146 so that the bubbles rise within the interior region of the tube and induce the fluid within this region to circulate from the lower region of the vessel to the upper region. This rising flow of fluid within tube 146 induces a corresponding, opposite circulation of fluid outside tube 146, from the upper region of vessel 102 to the lower region. This circulatory fluid flow, induced by the actions of the bubbles rising in fluid 104, causes the fluid in the upper and lower regions of vessel 102 to mix.

Coiled about tube 146 is a fluid conduit 148 coupled at a first end 150 to nutrient fluid inlet port 110 and coupled at a second end 152 to nutrient fluid outlet port 112. Conduit 148 couples fresh nutrient fluid from fresh nutrient fluid inlet 64 to fluid reservoir 12. Conduit 148 also serves to moderate the temperature of the fresh nutrient fluid by routing it through liquid 104, so that its addition to fluid reservoir 12 does not destabilize the reservoir's temperature.

If bubbler 128 and tube 146 were omitted from apparatus 100, the temperature of fluid 104 within vessel 102 would tend to stratify into thermal layers. The addition of tube 146 induces a well defined vertical fluid flow through vessel 102, causing fluid in the lower region to mix with fluid in the upper region, thereby eliminating thermal stratification.

Desirably, nutrient fluid reservoir 12 and humidifier/heat exchanger apparatus 100 are positioned above nutrient fluid heater 40. Although the function of heater 40 is primarily to heat the nutrient fluid passing therethrough to a predetermined temperature, excess heat rising from the top of this heater can advantageously be employed to warm the contents of media reservoir 12 and humidifier/heat exchanger apparatus 100. By this approach, a dual, efficient use is made of heater 40.

FLUID REPLACEMENT SYSTEM

In an exemplary embodiment, 30 c.c. of fluid 104 within humidifier/heat exchanger apparatus 100 is lost to the aerating gas per day as the gas is humidified. A novel apparatus 160 is provided to allow the controlled introduction of fluid into reservoir 102 to replace the this lost fluid.

Apparatus 160 includes a first check valve 162 having an inlet coupled to a replacement fluid inlet 164 through a sterile filter 166. A bag of fluid, such as deinoized reverse osmosis water, is coupled to fluid inlet 164. A second check valve 168 has an inlet coupled to the outlet of first check valve 162 and has an outlet coupled to conduit 124 through a conduit 170. A pump 172, such as a syringe pump, is coupled to the inlet of second check valve 168.

In operation, fluid is drawn from the replacement fluid inlet 164 through sterile filter 166 and check valve 162 into syringe 172 when the plunger 174 of the syringe is retracted. Check valve 168 assumes its closed position during this first phase of operation, thereby preventing the withdrawal of fluid or air from conduit 124. When piston 174 is thereafter pushed into syringe 172, the liquid contained therein is expelled into conduit 170 through second check valve 168. First check valve 162 and gas supply line check valve 120 assume their closed positions during this second phase of operation, thereby preventing the expulsion of fluid towards replacement fluid inlet 164 or air flow meter 118.

In an alternative embodiment, a hypodermic syringe may be filled with fluid at a remote location and operated to inject the fluid into conduit 124. Such daily breach of conduit 124, however, presents a risk of system contamination.

GAS TRAP

One source of reliability problems in bioreactor systems can be the bioreactor cartridge itself. The hollow fibers within the cartridge have an exceedingly small diameter and are susceptible to blockage by virtually any foreign material. Such blockages can be caused by tiny gas bubbles within the nutrient fluid, which bubbles can be produced either by surface turbulence of the fluid or by changes in the fluid pressure or temperature.

In the illustrated embodiment, nutrient fluid 18 is heated by heater 40 and is subsequently cooled during the rest of its travel. The amount of gas that can be dissolved within nutrient fluid 18 is dependent upon the fluid temperature: the lower the fluid temperature, the more gas can be dissolved therein. Accordingly, the volume of gas that can be dissolved within fluid 18 varies during its travel around circulatory path 54.

The temperature of the fluid entering oxygenator 34 is at its relatively lowest point throughout circulatory path 54. In an illustrative embodiment, this temperature may be on the order of 32 degrees Celsius. Fluid 18 is saturated with gas while at this low temperature. Consequently, the fluid leaving oxygenator 34 has the relatively highest concentration of gas throughout the system.

When nutrient fluid 18 is thereafter passed through heater 40, its temperature rises to approximately 37 degrees Celsius and the volume of gas that can be dissolved therein drops correspondingly. This excess gas appears in the form of bubbles at the outlet of heater 40. If these bubbles are allowed to propagate into the capillaries of bioreactor 16, they will occlude the capillaries and cause the cells being nourished through the occluded capillaries to die. Accordingly, it is important that the gas bubbles released during the heating process be removed from the fluid before it is introduced into bioreactor 16.

A novel air trap 42, shown in FIG. 5, is provided for this purpose. Air trap 42 comprises a chamber 180, a flow inlet 182, a flow outlet 184, a vent 186, and a float 188. Nutrient fluid from heater 40 is introduced at inlet 182 and floods the lower region of chamber 180. Flow outlet 184 couples this nutrient fluid to bioreactor 16.

Buoyant float 188 is disposed within chamber 180 and rises and falls with the chamber fluid level. Float 188 includes a member 190 adapted to occlude vent 186 when the level of the liquid within chamber 180 exceeds a certain height. When vent 186 is so occluded, bubbles in fluid 18 rise to the upper region of chamber 180 and collect, causing the volume of gas in this upper region to increase. This increasing volume of gas exerts a pressure on the fluid 18 in chamber 180, displacing it downwardly. After sufficient downward displacement of the level of fluid 18, member 190 has dropped sufficiently so that it no longer occludes vent 186, thereby allowing gas to escape therefrom. As gas escapes from the upper region of chamber 180, the level of fluid 18 rises, again causing member 190 to occlude vent 186. The cycle then begins again. Air trap 42 thus periodically "burps" a small burst of gas from the upper region of chamber 180 and out vent 186. The fluid supplied from flow outlet 184 to bioreactor 16 is substantially free of bubbles.

Returning again to FIG. 1, gasses released from vent 186 are routed to the upper region of fluid reservoir 12 through a conduit 190. This gas is vented to the atmosphere through a sterile vent 192 in the upper region or reservoir 12, which is provided to maintain reservoir 12 at atmospheric pressure.

By this gas trap arrangement, fluid supplied to bioreactor 16 is substantially free of bubbles, thereby avoiding blockages of bioreactor fibers. The illustrated structure performs this gas trapping function automatically and reliably without the need for operator supervision or intervention. Furthermore, it enables an inexpensive in-line fluid heater to be substituted for the costly incubators used in prior art systems.

An alternative embodiment 42' of a gas trap according to the present invention is shown in FIG. 6. In this embodiment, an electronic control circuit 192 senses the level of fluid in chamber 180' and opens a vent valve 196 whenever the level of fluid drops below a certain point. Control circuit 192 monitors the level of fluid in chamber 180' by means such a level sensing device 194. Level sensing device 194 can comprise a pointed optical conductor in conjunction with a photoelectric transmitter and receiver, as described earlier in connection with FIG. 3.

In the illustrated embodiment, the conical end of level sensor 194 is usually submerged within fluid 18 and control circuit 192 consequently maintains vent valve 196 in its closed state. As gas bubbles released from fluid 18 rise within chamber 180', the fluid level drops. When the fluid level drops below the conical end of level sensor 194, control circuit 192 switches vent valve 196 to its open state. With vent valve 196 open, the level of nutrient fluid quickly rises within chamber 180' and expels the collected gas. As soon as the fluid level has risen sufficiently to contact the conical end of level sensor 194, control circuit 192 closes vent valve 196 and the cycle repeats itself.

Of course, a variety of other level sensing techniques could be used in lieu of the illustrated pointed optical conductor.

In still other embodiments, the level detecting function can be omitted entirely. Instead, control circuit 192 can comprise a timer circuit which causes venting valve 196 periodically to open for a short time period. For example, control circuit 192 can cause valve 196 to open for one-half second every five seconds. During this brief period during which valve 196 is open, gas collected within the chamber can escape from the gas trap.

The "burping" of collected gas from gas trap 42 causes the nutrient flow through bioreactor 16 to hesitate for an instant while fluid flow is used to raise the liquid level in chamber 180. Some researchers have suggested that a pulsatile nutrient flow a bioreactor may stimulate cell growth, as it simulates more accurately the in-vivo environment from which the cells were taken. The duration of this hesitation is a function of several factors, including the buoyancy of float 188 and the response time of valve 196. A markedly pulsatile flow can be achieved by appropriate design of gas trap 42. In such cases, it is desirable to provide thermal insulation around trap 42 so that the nutrient fluid temperature does not drop below the desired value during its periodic pauses in chamber 180. In other embodiments, flow hesitations can be of higher frequency, but shorter duration so as to minimize disruption of the continuous fluid flow through bioreactor 16.

REMOTE MEDIA COLOR DETECTION

It is often desirable to monitor the color of the nutrient media fluid within reservoir 12. Sometimes an indicating agent, such as a chemical that changes color with pH, is added to nutrient fluid 18. By observing the color of nutrient fluid 18, certain aspects of its quality can be discerned. However, it is often desirable to prevent exposure of the cells being cultured to light. Accordingly, the fluid processing section of apparatus 10 is desirably placed within an enclosure that reduces exposure of the fluid circuitry to light. In the embodiment illustrated in FIG. 2, a housing 230 of smoky colored plastic covers this portion of the bioreactor system. It is impossible to determine the color of nutrient media 18 through this housing. Although housing 230 could be removed momentarily to allow inspection of the fluid color, this would perturb the thermal stability of the fluid circuitry components which is established by their extended operation within the housing.

To allow the color of the nutrient media to be determined during operation without removing housing 230, a color sensing apparatus 240 is employed. With reference to FIG. 7, apparatus 240 includes an optical fiber 242 having a first end 244 adjacent nutrient fluid reservoir 12. Optical fiber 242 extends to a second end 246 at a position outside smoky housing 230, preferably to a position on the front panel of apparatus 10, as shown in FIG. 2. Optical fiber 242 receives light propagating through nutrient fluid 18 within reservoir 12 and transmits this received light to second end 246 of fiber 242 at a position outside housing 230.

A light source 248 is disposed adjacent fluid reservoir 12 at a position opposite first end 244 of fiber 242 and illuminates nutrient fluid 18 within vessel 12. A switch 250 controllably couples light source 248 to a voltage source 252 so that the light source is energized only when so desired by the operator. The first end 244 of fiber 242 receives the light transmitted through fluid 18, which light has been colored by its transmission through the nutrient fluid. This colored light is transmitted through fiber 242 to the second end 246 at the position outside smoky housing 230. The color of nutrient fluid 18 can then be determined by inspecting second end 246 of fiber 242.

While the preceding has described preferred embodiments of the bioreactor system and several of the components used therein, it will be appreciated that the invention is not so restricted. For example, although the preceding discussion has assumed use of a hollow fiber bioreactor, a variety of other cell culture environments can alternatively be employed. Similarly, variations can be made in the illustrated structures without departing from the scope of the invention as defined in the appended claims and equivalents thereof. We claim as our invention all modifications coming within the scope and spirit of the following claims.

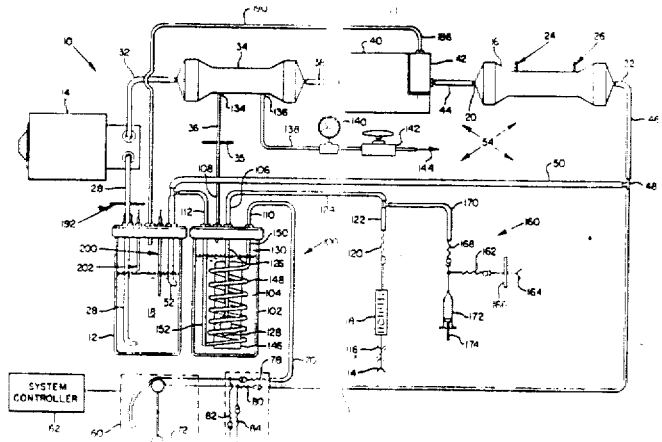

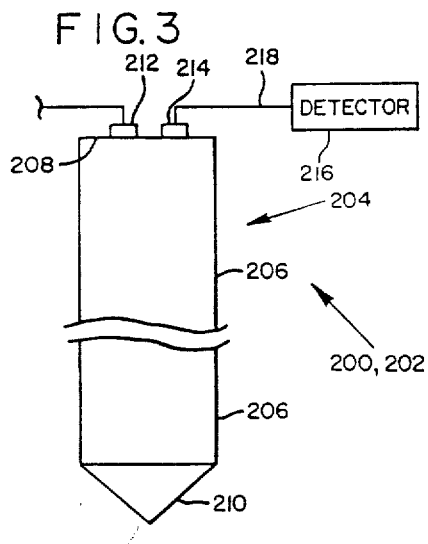
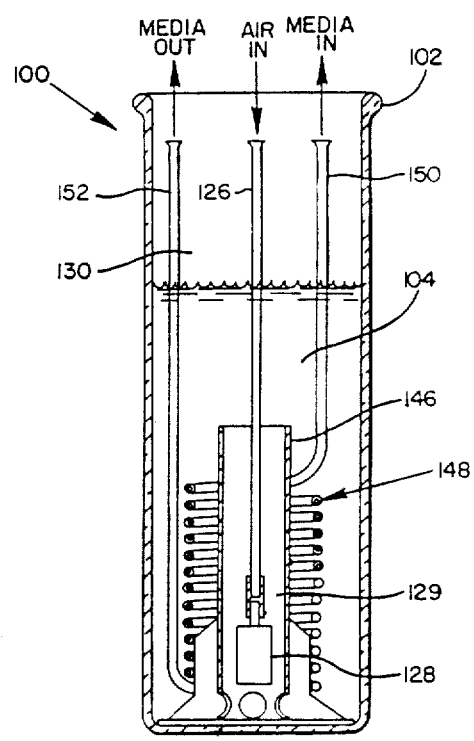
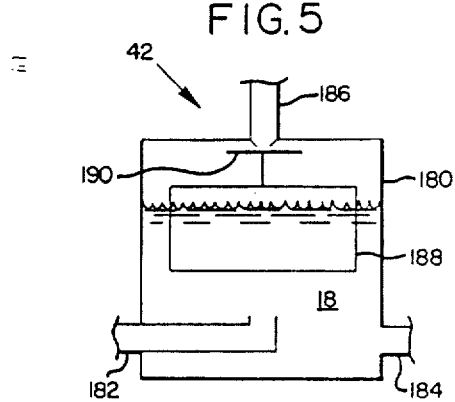
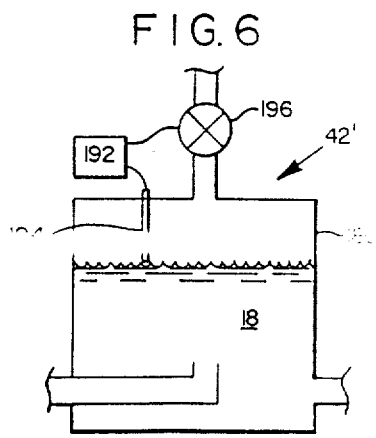
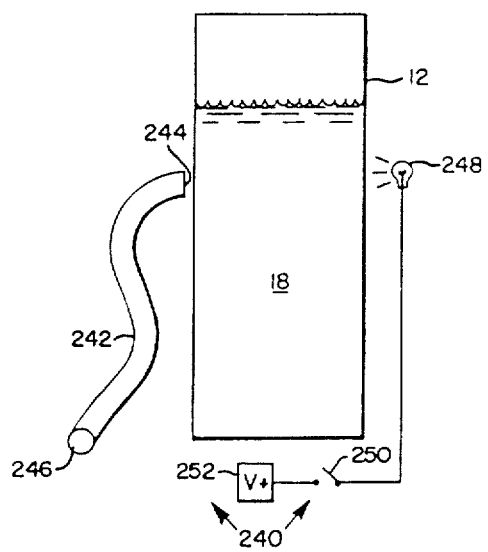

We claim:

1. A bioreactor system comprising:
   nutrient fluid reservoir means for containing nutrient fluid;
   bioreactor means for culturing biological materials;
   fluid inlet means for connection to a source of fresh nutrient fluid;
   fluid outlet means for connection to a used nutrient fluid drain;
   first pump means operatively coupled to the nutrient fluid reservoir means and the bioreactor means for causing nutrient fluid to recirculate from the nutrient fluid reservoir means through the bioreactor means and back into the nutrient fluid reservoir means;
   reversible second peristaltic pump means operatively coupled to the nutrient fluid means and being operable in first and second directions and having first and second tubes, the first tube coupling the fluid inlet means to a fresh fluid input circuit of the bioreactor system and the second tube coupling the fluid outlet means to a used fluid output circuit of the bioreactor means; and
   check valve means connected to the first and second tubes of the second pump means for:
   allowing the second pump means to pump fresh fluid from the fluid inlet means to the fresh fluid input circuit when operated in the first direction, but not pump fluid from the fluid outlet means to the used fluid output circuit when operated in said first direction; and
   allowing the second pump means to pump used fluid from the used fluid output circuit to the fluid outlet means when operated in the second direction, but not pump fluid from the fresh fluid input circuit to the fluid inlet means when operated in said second direction.

2. The bioreactor system of claim 1 in which the check valve means comprises:
   first check valve means serially connected in the first tube for allowing fluid flow in the fresh fluid input circuit when the pump means is operated in the first direction, but not when the pump means is operated in the second direction; and
   second check valve means serially connected in the second tube for allowing fluid flow in the used fluid output circuit when the pump means is operated in the second direction, but not when the pump means is operated in the first direction.

3. The bioreactor system of claim 2 in which the check valve means further comprises:
   third check valve means shunted across the first tube as it enters and exits the peristaltic pump means for providing a circulatory path for fluid in the first tube when the pump means is operated in the second direction; and
   fourth check valve means shunted across the second tube as it enters and exits the peristaltic pump means for providing a circulatory path for fluid in the second tube when the pump means is operated in the first direction.

4. A bioreactor system comprising:
   nutrient fluid reservoir means for containing nutrient fluid;
   bioreactor means for culturing biological materials;
   pump means operatively coupled to said nutrient fluid reservoir means and said bioreactor means for causing nutrient fluid to flow from the nutrient fluid reservoir means through the bioreactor means;
   gas inlet means for allowing the introduction of gas;
   humidifier means coupled to the gas inlet means for humidifying the gas introduced therethrough;
   oxygenator means included in a fluid circuit comprised of the aforesaid nutrient fluid reservoir means, bioreactor means and pump means and also coupled to the humidifier means for aerating the nutrient fluid with humidified gas from the humidifier means;
   said humidifier means further including means for generating bubbles in the humidifying fluid for humidifying the gas contained within said bubbles and for inducing circulation in the humidifying fluid to prevent the thermal stratification thereof, the humidifier means also including heat exchanger means comprised of a tube immersed in the humidifying fluid through which nutrient fluid flows to the reservoir means.

5. The bioreactor system of claim 4 which further includes:
   heater means disposed beneath the humidifier means for heating the nutrient fluid routed therethrough and for warming the humidifying fluid.

6. A bioreactor system comprising:
   nutrient fluid reservoir means for containing nutrient fluid;
   bioreactor means for culturing biological materials;
   pump means operatively coupled to said nutrient fluid reservoir means and said bioreactor means for causing nutrient fluid to flow from the nutrient fluid reservoir means through the bioreactor means; and
   remote sensor means coupled to a fluid circuit comprised of the aforesaid nutrient fluid reservoir means, bioreactor means and pump means for allowing the color of the nutrient fluid to be determined at a location remote from said nutrient fluid;
   said remote sensor means comprising a passive optical element operated without electricity for permitting the color of the nutrient fluid to be determined at a location remote therefrom.

* * * * *

UNITED STATES PATENT AND TRADEMARK OFFICE
CERTIFICATE OF CORRECTION

PATENT NO. : 4,894,342

DATED : January 16, 1990

INVENTOR(S) : Perry W. Guinn and Gary N. Mills

It is certified that error appears in the above-identified patent and that said Letters Patent is hereby corrected as shown below:

The title page showing the illustrative figure should be deleted to appear as per attached title page.

The sheets of Drawing consisting of Figs 1-7 should be deleted. The Sheets of Drawing consisting of Fig. 1-8, should be added as per attached Sheets.

Column 9, line 31, "or" should read --of--.

Signed and Sealed this

Fifth Day of May, 1992

Attest:

DOUGLAS B. COMER

Attesting Officer

Acting Commissioner of Patents and Trademarks

United States Patent [19]

Guinn et al.

[11] Patent Number: 4,894,342
[45] Date of Patent: Jan. 16, 1990

[54] BIOREACTOR SYSTEM

[75] Inventors: Perry W. Guinn, Oregon City; Gary N. Mills, Gladstone, both of Oreg.

[73] Assignee: C. D. Medical, Inc., Miami Lakes, Fla.

[21] Appl. No.: 909,962

[22] Filed: Sep. 22, 1986

Related U.S. Application Data

[63] Continuation-in-part of Ser. No. 862,014, May 12, 1986.

[51] Int. Cl.⁴ .................. C12M 1/04; C12M 1/14; C12M 1/34
[52] U.S. Cl. .................. 435/291; 435/240.242; 435/284; 435/285; 435/313; 435/813; 435/818
[58] Field of Search .................. 435/240.242, 813, 818, 435/284, 285, 291, 313

[56] References Cited

U.S. PATENT DOCUMENTS 3,407,120 10/1968 Weiss et al.
3,734,851 5/1973 Matsumura
3,821,087 6/1974 Knazek et al.
4,087,327 5/1978 Feder et al.
4,116,778 9/1978 Belousov et al. .................. 435/291
4,266,026 5/1981 Breslau
4,335,215 5/1982 Tolbert et al.
4,411,651 10/1983 Schulman
4,440,853 4/1984 Michaels
4,530,759 7/1985 Schal
4,559,299 12/1985 Rotman .................. 435/240.242
4,725,148 2/1988 Endo et al. .................. 435/291

FOREIGN PATENT DOCUMENTS 60-126075 7/1985 Japan
WO86/02378 4/1986 PCT Int'l Appl.
WO86/02379 4/1986 PCT Int'l Appl.

OTHER PUBLICATIONS

Endotronics brochure "ACUSYST-JR." 1986, 8500 Evergreen Blvd., Coon Rapids, MN 55433.
Endotronics brochure "ACUSYST-M".
Endotronics brochure "ACUSYST-S".
AMICON brochure, publication No. 492, 17 Cherry Hill Drive, Danvers, MA 01923.
"VIRTIS Omni-Culture Laboratory Fermenter" brochure, 1984/10M, Gardner, NY 12525.
Ventrex "Cellift" brochure, 1986, 217 Reed St., Portland, ME 04103.
Queue Systems brochure "The New Bioreactor System for Fermentation and Cell Culture" 1986, Parkersburg, WV, 26102, Box 1901.
Queue Systems brochure "New Technologies and Products for Cell Culture", 1985, Box 1901, Parkersburg, WV, 26102.
Queue Systems brochure (untitled) discussing Hybrinet Hollow Fiber Perfusion Bioreactor, 1986.

(List continued on next page.)

Primary Examiner—Barry S. Richman
Assistant Examiner—Timothy M. McMahon

[57] ABSTRACT

An improved bioreactor system for culturing cell products is disclosed in which novel system components are employed to reduce cost and increase reliability. The system includes a simple in-line heater for heating the nutrient fluid, thereby obviating the need for an expensive incubator. Gas bubbles formed during the heating of the nutrient fluid are removed by a novel gas trap that requires no operator intervention. A humidifier humidifies an aerating gas before it is passed through an oxygenator, thereby preventing water within the nutrient fluid from evaporating, with a consequent increase in nutrient fluid concentration. The operation of the humidifier is efficiently combined with that of a nutrient fluid heat exchanger so that a pump is not required to circulate the heat exchanger water bath. The system further includes a valve and pump arrangement whereby fresh nutrient fluid can periodically be introduced and spent nutrient fluid periodically drained without operator intervention. Observation of the color of the nutrient fluid from a concealed location within the bioreactor enclosure is also made possible.

6 Claims, 4 Drawing Sheets